United States Patent [19]
Hiskett et al.

[11] Patent Number: 5,861,179
[45] Date of Patent: Jan. 19, 1999

[54] PHARMACEUTICAL COMPOSITION OF LAMOTRIGINE

[75] Inventors: Simon Philip Hiskett; Susan Ann Taylor, both of Kent, United Kingdom

[73] Assignee: The Wellcome Foundation Limited, Middlesex, Great Britain

[21] Appl. No.: 849,070

[22] PCT Filed: Dec. 7, 1995

[86] PCT No.: PCT/GB95/02865

§ 371 Date: Jun. 26, 1997

§ 102(e) Date: Jun. 26, 1997

[87] PCT Pub. No.: WO96/17611

PCT Pub. Date: Jun. 13, 1996

[30] Foreign Application Priority Data

Dec. 7, 1994 [GB] United Kingdom ............... 9424766

[51] Int. Cl.⁶ .................................................. A61K 31/53
[52] U.S. Cl. .................... 424/499; 424/489; 424/501; 514/242
[58] Field of Search ...................... 424/499, 501, 424/489; 514/242

[56] References Cited

U.S. PATENT DOCUMENTS

| | | | |
|---|---|---|---|
| 3,637,688 | 1/1972 | Rees et al. ........................... | 260/249.9 |
| 4,486,354 | 12/1984 | Baxter et al. ........................ | 260/465 E |
| 4,602,017 | 7/1986 | Sawyer et al. ........................ | 514/242 |
| 5,556,639 | 9/1996 | Fielden ................................. | 424/480 |
| 5,591,746 | 1/1997 | Miller et al. ......................... | 514/255 |
| 5,597,828 | 1/1997 | Miller et al. ......................... | 514/275 |
| 5,635,507 | 6/1997 | Miler et al. .......................... | 514/255 |
| 5,698,226 | 12/1997 | Fielden ................................. | 424/480 |
| 5,712,227 | 1/1998 | Miller et al. ......................... | 514/235.8 |

FOREIGN PATENT DOCUMENTS

| | | |
|---|---|---|
| 2 700 114 | 7/1994 | France . |
| 2 702 149 | 9/1994 | France . |
| 2 278 057 | 11/1994 | United Kingdom . |
| 93 16700 | 9/1993 | WIPO . |
| 94 13296 | 6/1994 | WIPO . |
| 94 20108 | 9/1994 | WIPO . |
| 94 21260 | 9/1994 | WIPO . |
| 94 21261 | 9/1994 | WIPO . |

*Primary Examiner*—Joseph K. McKane
*Attorney, Agent, or Firm*—Bacon & Thomas, PLLC

[57] ABSTRACT

The present invention relates to a pharmaceutical formulation of lamotrigine, pharmaceutically acceptable salts thereof and the preparation of such a formulation.

8 Claims, No Drawings

PHARMACEUTICAL COMPOSITION OF LAMOTRIGINE

This application is a 371 of PCT/GB45/02865 filed Dec. 7, 1995.

The present invention relates to a pharmaceutical formulation of lamotrigine and pharmaceutically acceptable acid addition salts thereof. The invention also relates to the preparation of such a formulation.

Lamotrigine is 3,5-diamino-6-(2,3-dichlorophenyl)-1,2,4-triazine. It is disclosed in EP-A-0021121. Lamotrigine is useful for the treatment of epilepsy. No powder formulation of lamotrigine or one of its salts is currently available.

Pharmaceutical formulations in powder form can be prepared by a fluid bed granulating process or spray granulation. However, such processes represent a complex interaction of processing variables.

We have now prepared a number of powder formulations of lamotrigine. Only one type of formulation, however, proved to be entirely satisfactory. Accordingly, the present invention provides a pharmaceutical formulation which comprises:

(a) from 0.5 to 50% by weight of lamotrigine or a pharmaceutically acceptable acid addition salt thereof,
(b) from 15 to 50% by weight of lactose,
(c) from 15 to 50% by weight of starch,
(d) from 0.5 to 15% by weight of crystalline cellulose, and
(e) from 5 to 15% by weight of polyvinylpyrrolidone, and which is in the form of a free-flowing powder of granules having the following properties:

(i) no granules have a particle size of greater than 850 μm,
(ii) at least 90% by weight of the granules have a particle size of from 75 to 850 μm,
(iii) the granules disintegrate within 30 minutes according to the Disintegration Test of The Pharmacopoeia of Japan, twelfth edition, 1991, and
(iv) at least 90% by weight of the lamotrigine or lamotrigine salt in the granules dissolves within 30 minutes when the granules are subjected to the Dissolution Test, method 2 (paddle method) of The Pharmacopoeia of Japan, twelfth edition, 1991.

The Disintegration Test of The Pharmacopoeia of Japan is a method to determine the resistance or disintegration of solid preparations for internal use in the test fluids. The test utilizes an apparatus consisting of a basket-rack assembly, a beaker, a suitable thermostatic arrangement for heating and a motor. The test liquid may be acidic, basic or water.

In the procedure, the basket-rack assembly is immersed in a liquid in the beaker and the apparatus is adjusted so as to raise and lower the basket smoothly at a constant frequency of 29–32 cycles per minute through a distance of 53–57 millimeters. At the lowest point of the downward stroke, the wire mesh must be 25 millimeters distant from the bottom of the beaker and the volume of the fluid in the beaker is such that at the lowest point of the downward stroke, the top of the basket is unlevel with the surface of the liquid. The temperature of the liquid is maintained at 37° plus or minus 2 during the test.

The Dissolution Test is a method to test the dissolution of active ingredient from solid preparations for internal use. In the paddle method described, the testing assembly includes a rotary shaft with a blade. The blade and rotary shaft are inserted in a test solution and the sample is allowed to sink to the center of the vessel containing the test solution and the test performed.

The formulation of the invention is provided by a process which comprises spray-granulating:

(a) from 0.5 to 50% by weight of lamotrigine or a lamotrigine salt,
(b) from 15 to 50% by weight of lactose,
(c) from 15 to 50% by weight of starch, and
(d) from 0.5 to 15% by weight of crystalline cellulose, in the presence of, as a binder:
(e) from 5 to 15% by weight of polyvinylpyrrolidone.

The granules of which the powder of the invention is composed are agglomerates. The lamotrigine or lamotrigine salt is provided on particles of lactose and starch which each act as an adsorbent bulking agent. A homogenous powder mixture comprising components (a) to (d) may be formed as a pre-blend prior to starting the spray granulation procedure. The presence of the lactose aids the formation of this pre-blend. The crystalline cellulose confers disintegrant and dissolution properties on the granules. The polyvinylpyrrolidone acts as a binder.

Any suitable lamotrigine salt which is a pharmaceutically acceptable acid addition salt can be used. Preferred salts are the methanesulphonate and isethionate salts. These salts can be made by reacting lamotrigine as the free base with the appropriate acid.

Preferably up to 98% by weight of the granules of the invention have a particle size of from 75 to 850 μm. At least 92% by weight of the granules may have such a particle size, for example from 92 to 95% by weight of the granules. Preferably no more than 5% by weight of the granules have a particle size greater than 500 μm, for example no more than 3% by weight. Desirably, no granules at all have a particle size greater than 500 μm. Particle size is determined by the Particle Size Distribution Test for Powders, The Pharmacopoeia of Japan, twelfth edition, 1991.

Typically, at least 90% by weight of the lamotrigine or lamotrigine salt in the granules is dissolved within 15 minutes according to the Dissolution Test, method 2 (paddle method). The amount of lamotrigine dissolved is determined by an appropriate physicochemical technique, for example by ultraviolet (UV) analysis or by high pressure liquid chromatography (hplc).

The powder of the invention is generally dust-free. It is preferably white although it may be white to off-white. A colourant could be present, though. It is free-flowing, as may be determined by the eye. Typically the bulk density of the powder is from 0.3 to 0.6 g/cm$^3$, for example from 0.35 to 0.50 g/cm$^3$ or from 0.36 to 0.40 g/cm3. Residual moisture levels are generally from 0.5 to 5.0% by weight, for example from 1 to 3% by weight.

Preferred formulations contain from 0.5 to 30% by weight of lamotrigine or a lamotrigine salt. Formulations may thus contain from 0.5 to 20% by weight, for example from 0.5 to 15% by weight or from 1 to 10% by weight, of lamotrigine or a lamotrigine salt. Particularly preferred are formulations containing 1%, 2%, 5% or 10% by weight of lamotrigine or a lamotrigine salt.

The amounts of lactose and starch in the formulations are greater the smaller the amount of lamotrigine or lamotrigine salt that is present. The starch is preferably corn starch. Suitable amounts of lactose and starch may be from 15 to 45% by weight, for example from 30 to 45% by weight or from 35 to 45% by weight or from 40 to 45% by weight. Preferably the amount of lactose is 70 to 130%, for example 90 to 110%, the amount of starch. Typically, the amounts of lactose and starch are the same.

The powders of the invention may contain from 3 to 8% by weight, for example from 3.5 to 6% by weight, of crystalline cellulose. Powders containing 5% by weight of crystalline cellulose are preferred.

Preferably the amount of polyvinylpyrrolidone present is from 5 to 10% by weight, for example from 6 to 9% by weight, of the formulation. Powders containing 8% by weight of polyvinvylpyrrolidone are preferred.

A preferred formulation of the invention comprises:

(a') from 0.5 to 15% by weight of lamotrigine or a lamotrigine salt, (b') from 35 to 45% by weight of lactose, (c') from 35 to 45% by weight of starch, (d') from 3.5 to 6% by weight of crystalline cellulose, and (e') from 6 to 9% by weight of polyvinylpyrrolidone.

An especially preferred formulation comprises 1% by weight of lamotrigine, 43% by weight of each of lactose and starch, 5% by weight of crystalline cellulose and 8% by weight of polyvinylpyrrolidone. Another especially preferred formulation comprises 10% by weight of lamotrigine, 38.5% by weight of each of lactose and starch, 5% by weight of crystalline cellulose and 8% by weight of polyvinylpyrrolidone.

A formulation of the invention is prepared by a process which comprises spray-granulating the lamotrigine or lamotrigine salt, lactose, starch, crystalline cellulose in the presence of, as a binder, the polyvinylpyrrolidone. The lamotrigine salt, lactose, starch and crystalline cellulose are each provided as powders having particle sizes, for example average particle sizes, well below 850 $\mu$m and, indeed, below 200 $\mu$m. These four components may be pre-blended as a uniform mixture prior to the spray granulation step.

A solution of polyvinylpyrrolidone is prepared as a binder solution. The solution may be an aqueous or aqueous/ethanolic solution. A proportion of the polyvinylpyrrolidone, for example from 30 to 60% by weight or more especially 50% by weight, may be pre-blended with the lamotrigine or lamotrigine salt, lactose, starch and crystalline cellulose.

A fluid bed granulation process is employed to obtain the powder of the invention. A rotary-type fluid granulator is typically used. The lamotrigine or lamotrigine salt, lactose, starch and crystalline cellulose are introduced in powder form into the granulator, for example as a pre-blended mixture. The binder solution is sprayed onto the fluidising powder. The particles of the fluidising powder adhere to one another. The desired granules form. The conditions under which granulation is effected can be adjusted as appropriate.

The granules thus obtained may be sieved to ensure that the appropriate particle size requirements are met. Thus, the granules may be sieved through a sieve of 850 $\mu$m mesh size to ensure no granules having a particle size of greater than 850 $\mu$m are present. Further, the granules may be sieved through a sieve of 50 $\mu$m mesh size to ensure that no more than 5% by weight of the granules have a particle size greater than 500 $\mu$m. Yet further, the granules may be sieved through a sieve of 75 $\mu$m mesh size. Indeed, the granules obtained from the granulator may be passed to a sieve stack fitted with 850, 500 and 75 $\mu$m sieves. Oversized and undersized materials are rejected.

The lamotrigine or lamotrigine salt employed as a starting material typically has a particle size of 125 $\mu$m or less. The starting lactose generally has a particle size of below 250 $\mu$m, especially 200 $\mu$m or less such as from 50 to 200 $\mu$m. The lactose may be an anhydrous lactose, for example direct compression lactose such as Lactose DCL21, or lactose monohydrate.

The particle sizes of Lactose DCL21 and another grade of lactose that can be used, Lactose DMV200, are as follows:

| DCL 21 | Approx | DCL 200 II | Approx |
|---|---|---|---|
| >50 $\mu$m | 85% | >45 $\mu$m | 40–50% |
| >150 $\mu$m | 40% | >63 $\mu$m | 17 . 22% |
| >250 $\mu$m | 5% | >100 $\mu$m | 1–7% |
| >355 $\mu$m | 0% | >160 $\mu$m | 0–1% |
| | | >250 $\mu$m | 0% |

The starch may be rice, wheat or corn starch. Corn starch is alternatively termed maize starch and is preferred. A powder of starch of a particle size of from 30 to 150 $\mu$m is typically used as a starting material. The starch may be a partially pregelatinised starch such as Starch 1500 manufactured by Colorcon, Indianapolis, Ind. 46218, US, or a fully gelatinised starch such as National 1551.

The crystalline cellulose typically is a powder of, for example, an average particle size of from 40 to 100 $\mu$m such as from 50 to 90 $\mu$m. A suitable crystalline cellulose is Avicel PH 102 having an average particle size of 90 $\mu$m. Crystalline cellulose is alternatively called microcrystalline cellulose.

Any suitable polyvinylpyrrolidone capable of acting as a binder can be employed. The polyvinylpyrrolidone may be a linear polymer of 1-vinyl-2-pyrrolidone having an average molecular weight of about 40000, such as Povidone K30. Alternatively, a linear polymer of 1-vinyl-2-pyrrolidone having an average molecular weight of about 1200000, such as Povidone K90, may be employed.

The powder that is produced by spray granulation and, if necessary, subsequent sieving is then introduced into a container which is then closed. The container may be sealed. It may be a single-dose or multi-dose container. The container may be jar, bag or sachet. Sachets, especially foil sachets, are particularly suitable.

The following Examples illustrate the invention.

EXAMPLE 1

1 Kg of each of five powders was prepared by spray granulation. The formula for each powder is as follows:

Formula A (comparison)
Lamotrigine 125 $\mu$m . . . 1.0% by weight
Lactose Fastflo . . . 91.0% by weight
Povidone K30 British
Pharmacopoeia (BP) . . . 8.0% by weight Lamotrigine 125 $\mu$m is lamotrigine having particle sizes up to 125 $\mu$m. Lactose Fastflo is an anhydrous spray-dried lactose manufactured by Wisconsin Dairies, Baraboo, Wis. 53913, U.S..

Formula B (comparison)
Lamotrigine 125 $\mu$m . . . 1.0% by weight
Lactose Fastflo . . . 43.0% by weight
Lactose DCL21 . . . 43.0% by weight
Povidone K30 BP . . . 8.0% by weight
Hydroxypropylcellulose low substitution
(LHPC-11) . . . 5.0% by weight Formula C (invention)
Lamotrigine 125 $\mu$m . . . 1.0% by weight
Lactose DCL21 . . . 43.0% by weight
Pregelatinised Maize (Corn) Starch
BP/USNF (Starch 1500) . . . 43.0% by weight
Microcrystalline cellulose BP
(Avicel PH 102) . . . 5.0% by weight
Povidone K30 BP . . . 8.0% by weight Formula D (comparison)
Lamotrigine 125 $\mu$m . . . 1.0% by weight
Pregelatinised Maize (Corn) Starch
BP/USNF (Starch 1500) . . . 86.0% by weight Hydroxypropylcellulose
low substitution (LHPC-11) . . . 5.0% by weight
Povidone K30 BP . . . 8.0% by weight Formula E (comparison)
Lamotrigine 125 μm . . . 1.0% by weight
Pregelatinised Maize Starch
BP/USNF (Starch 1500) . . . 91.0% by weight
Povidone K30 BP . . . 8.0% by weight Formula C was spray-granulated as follows as 2×5 kg sub-lots:

1. A Povidone binder solution was prepared and stored at room temperature.

2. The pregelatinised starch was passed through a 250 μm sieve to remove any large agglomerates.

3. The lamotrigine, lactose, starch and Avicel PH102 were pre-blended in a Collette mixer as a precautionary measure to facilitate uniform lamotrigine distribution.

4. The powder was spray-granulated in a Glatt GPCG5 granulator using a Schlick spray gun of nozzle aperture 1.2 mm utilising atomising air at a pressure of 2 bars. The binder solution pumping rate was approximately 90 ml per minute. The inlet air temperature was controlled at 72° C. and an air volume of between 150–250 m³ per hour was utilised to provide sufficient fluidisation to allow drying and granulation to occur simultaneously. The drier bags were shaken for approximately 6 seconds at 1.5 minute intervals to remove fine powder.

5. During granulation the product temperature was recorded. This temperature was typically 32°–340° C. but once spraying had been completed this rose shortly afterwards to 45°–50° C. indicating that final drying was occurring. The overall process time was of the order of 1 hour per sub-lot.

6. The two sub-lots of granules were then blended in a large polythene bag and finally sieved through a Russell Finex sieve using screen of 710 μm and 100 μm to remove under and over-sized components of the granules.

Formulae A, B, D and E were spray-granulated in analogous fashion. Powders of free-flowing white granules were obtained in the case of formulae A to C and E. Formula D gave a powder which was severely overmassed. A substantial proportion of particles were oversize. This powder was not therefore satisfactory and was not tested further. The properties of the powders obtained from formulae A to C and E are as follows:

| Formula | A | B | C | E |
|---|---|---|---|---|
| Yield % | 91.8 | 80.5 | 87.4 | 86.3 |
| Moisture % | 0.68 | 1.21 | 2.46 | 0.65 |
| Untamped Bulk Density g/cm³ | 0.40 | 0.53 | 0.37 | 0.50 |
| % by weight of granules over 850 μm in size | 0% | 0% | 0% | 0% |
| % by weight of granules over 500 μm in size | 4.8 | 1.2 | 8.1 | 2.0 |
| % by weight of granules over 75 μm in size | 94.8 | 97.8 | 92.5 | 97.4 |
| Disintergration Test* | Complies | Complies | Complies | Complies |

*Disintegration Test, The Pharmacopoeia of Japan, twelfth edition, 1991.

Initially, 9.8% by weight of the powder obtained from formula B did not pass through a 500 μm sieve. The powder was therefore resieved through a 500 μm sieve. Subsequent sieve analysis showed that only 1.2% of the powder then did not pass through a 500 μm test sieve. Different 500 μm sieves were used for the resieving and the subsequent testing, which accounts for why some powder still did not pass through the 500 μm test sieve.

EXAMPLE 2

General

The effect of temperature, humidity and artificial light was studied on the stability of the powders obtained in Example 1 according to formulae A to C and E. The powders were stored for two months at 40° C. and 75% relative humidity (R.H.) in both amber glass bottles closed with plastic caps and open amber glass bottles. They were also stored at 50° C. and 60° C. for 2 months in amber glass bottles closed with plastic caps. Further, they were stored at 25° C. under artificial light conditions (1000 lux) for up to 1.2 million lux.hr total irradiation.

Test Items

The following parameters were monitored to evaluate the stability of the formulations:

1. Appearance

2. Loss on drying

Conditions of 60° C. in vacuo for 3 hours were employed for formulae A and B. Conditions of 60° C. in vacuo for 6 hours were employed for formulae C and E. These test conditions were decided with reference to the test conditions of lactose and starch in The Pharmacopoeia of Japan, twelfth edition, 1991.

3. Assay and related substances

A lamotrigine assay and a purity test were conducted by high pressure liquid chromatography (hplc).

4. Dissolution test

Dissolution of the powders was studied using the Dissolution Test, method 2 (paddle method) of The Pharmacopoeia of Japan, twelfth edition, 1991. The time points of sampling were 15, 30 and 45 min and 0.1N hydrochloric acid was used as the test solution. Lamotrigine was detected by ultraviolet absorption.

Results

1. Appearance

Under 40° C. and 75% R.H., all of the powders in open glass bottles formed lumps in the high humidity and had turned pale yellowish white in colour. The colour of, in particular, the powder of formula B easily changed under severe conditions compared to the colour of the other particles. Results are shown in Tables 1 to 5 below.

2. Loss on drying

Formula E was the most hygroscopic powder. The results are shown in Tables 1 to 5.

3. Assay and related substances

From the degradation point of view, the most stable powder was that obtained from formula E and the most unstable powder was that from formula A under the high humidity conditions such as 40° C., 75% R.H., open glass bottle conditions.

4. Dissolution test

All of the formulations showed rapid dissolution. More than 90% of the lamotrigine in each powder was dissolved within 15 minutes.

TABLE 1

Granules Stored under 40° C, 75% R.H. Conditions
(Container: Closed Glass Bottles).

| Test Items | Form-ula | Storage Period | | |
|---|---|---|---|---|
| | | Initial | 1 month | 2 months |
| Appearance | A | White powder | White powder | White powder |
| | B | White powder | White powder | Pale yellowish white powder |
| | C | White powder | White powder | White powder |
| | E | White powder | White powder | White powder |
| Loss on Drying (n = 3, % by weight) | A | 1.15 ± 0.10* | 1.40 ± 0.01 | 1.23 ± 0.02 |
| | B | 1.63 ± 0.16 | 1.67 ± 0.02 | 1.81 ± 0.07 |
| | C | 4.29 ± 0.12 | 4.98 ± 0.17 | 4.78 ± 0.01 |
| | E | 7.27 ± 0.16 | 7.44 ± 0.07 | 7.24 ± 0.02 |

*Mean ± S.D.

TABLE 2

Granules Stored under 40° C, 75% R.H. Conditions
(Container: Open Glass Bottles).

| Test Items | Form-ula | Storage Period | | |
|---|---|---|---|---|
| | | Initial | 1 month | 2 months |
| Appearance | A | White powder | Pale yellowish white cake | Pale yellowish white cake |
| | B | White powder | Pale yellowish white cake | Pale yellowish white cake |
| | C | White powder | Pale yellowish white cake | Pale yellowish white cake |
| | E | White powder | Pale yellowish white cake | Pale yellowish white cake |
| Loss on Drying (n = 3, % by weight) | A | 1.15 ± 0.10* | 1.03 ± 0.31 | 2.15 ± 0.02 |
| | B | 1.63 ± 0.16 | 1.05 ± 0.03 | 2.65 ± 0.03 |
| | C | 4.29 ± 0.12 | 3.69 ± 0.20 | 8.24 ± 0.09 |
| | E | 7.27 ± 0.16 | 6.66 ± 0.24 | 14.32 ± 0.03 |

*Mean ± S.D.

TABLE 3

Granules Stored under 50° C. Condition
(Container: Closed Glass Bottles).

| Test Items | Form-ula | Storage Period | | |
|---|---|---|---|---|
| | | Initial | 1 month | 2 months |
| Appearance | A | White powder | White powder | White powder |
| | B | White powder | White powder | White powder |
| | C | White powder | White powder | White powder |
| | E | White powder | White powder | White powder |
| Loss on Drying (n = 3, % by weight) | A | 1.15 ± 0.10* | 0.94 ± 0.11 | 0.59 ± 0.15 |
| | B | 1.63 ± 0.16 | 1.57 ± 0.19 | 1.05 ± 0.13 |
| | C | 4.29 ± 0.12 | 4.12 ± 0.11 | 3.76 ± 0.15 |
| | E | 7.27 ± 0.16 | 7.04 ± 0.12 | 6.57 ± 0.14 |

*Mean ± S.D.

TABLE 4

Granules Stored under 60° C. Condition
(Container: Closed Glass Bottles).

| Test Items | Form-ula | Storage Period | | |
|---|---|---|---|---|
| | | Initial | 1 month | 2 months |
| Appearance | A | White powder | White powder | White powder |
| | B | White powder | Pale yellowish white powder | Pale yellowish white powder |
| | C | White powder | Pale yellowish white powder | Pale yellowish white powder |
| | E | White powder | White powder | White powder |
| Loss on Drying (n = 3, % by weight) | A | 1.15 ± 0.10* | 0.58 ± 0.11 | 0.42 ± 0.03 |
| | B | 1.63 ± 0.16 | 0.75 ± 0.14 | 0.64 ± 0.08 |
| | C | 4.29 ± 0.12 | 3.61 ± 0.11 | 3.13 ± 0.04 |
| | E | 7.27 ± 0.16 | 6.71 ± 0.17 | 6.03 ± 0.03 |

*Mean ± S.D.

TABLE 5

Granules Stored under 25° C., 1000 lux
Irradiation (Container: Glass Dishes).

| Test Items | Form-ula | Storage Period | | |
|---|---|---|---|---|
| | | Initial | 0.6 million lux.hr | 1.2 million lux.hr |
| Appearance | A | White powder | White powder | White powder |
| | B | White powder | White powder | White powder |
| | C | White powder | White powder | White powder |
| | E | White powder | White powder | White powder |
| Loss on Drying (n = 3, % by weight) | A | 1.15 ± 0.10* | —** | 1.43 ± 0.06 |
| | B | 1.63 ± 0.16 | — | 1.90 ± 0.03 |
| | C | 4.29 ± 0.12 | — | 5.34 ± 0.05 |
| | E | 7.27 ± 0.16 | — | 9.03 ± 0.07 |

*Mean ± S.D.
**Not examined

Conclusion

Formula A (comparison)

The powder of this formulation was stable under high temperature conditions without humidity. Under high humidity conditions, however, it became slightly unstable.

Formula B (comparison)

The powder of this formulation was stable under high temperature conditions without humidity. However, it changed colour the most easily. Under high humidity conditions it became slightly unstable.

Formula C (invention)

The powder of this formulation was stable under high temperature conditions without humidity. It was also stable under high humidity conditions.

Formula E (comparison)

The powder of this formulation was stable under high temperature conditions without humidity. It was also stable under high humidity conditions. Under high humidity conditions, however, it absorbed the most moisture.

EXAMPLE 3

Powders were prepared by spray granulation of each of the following formulae:

| | Formula 1 | Formula 2 |
|---|---|---|
| Lamotrigine 125 μm | 1.0% by weight | 10.0% by weight |
| Lactose, DMV 200 mesh | 43.0% by weight | 38.50% by weight |

-continued

|            | Formula 1       | Formula 2        |
|------------|-----------------|------------------|
| Starch 1500 | 43.0% by weight | 38.50% by weight |
| Avicel PH102 | 5.0% by weight | 5.0% by weight   |
| Povidone K30 | 8.0% by weight | 8.0% by weight   |

50 g of lamotrigine 125 μm and 2150 g of each of Lactose DMV 200 mesh and Starch 1500 (Formula 1) or 500 g of lamotrigine 125 μm and 1925 g of each of Lactose DMV 200 mesh and Starch 1500 (Formula 2) were mixed together with 250 g of Avicel PH102 and 200 g of Povidone K30 in a Collette Planetary mixer for 3 minutes. An approximately uniform pre-blend of powders is thus produced.

Separately, 200 g of Povidone K30, the second half of the Povidone K30, was dissolved in 600 ml of demineralised water. That was then made up to 1000 ml to give a 20% solids solution. This was used as the granulating solution.

The pre-blend of powders was added to a Freund SFC rotor granulator. This is a type of fluid bed granulator and provides a rotary type fluidization action on powders in order to achieve a suitable granule distribution. The granulating solution was sprayed onto the fluidizing powders as a fine mist via an air type spray gun system. The addition of the granulating solution in this way resulted in the powders adhering together to form suitably sized granule particles. The process was continued until all the granulating solution had been added and the granules were of a suitable size.

More especially the following parameters were used on the Freund SFC granulator:

1) Inlet air temperature 80° C.
2) Rotor speed 300 rpm
3) Agitator speed 450 rpm
4) Chopper speed 1500 rpm
5) Inlet air Volume 2.9 m$^3$/hr
6) Atomizing air pressure 4 kg/cm$^2$
7) Spray Nozzle Size 1.8 mm
8) Spray rate 45 g/min Using these parameters the required granules were produced employing:

1) Inlet air temperature 75°–80° C.
2) Outlet air temperature 28°–32° C.
3) Product temperature 28°–35° C.
4) Air Volume 2.9–3.0 m$^3$/hr
5) Spray rate 40–43 g/min
6) Time to granulate powders 22 min
7) Time to dry granule 11 min The prepared granules were then passed through a sieve fitted with 850, 500 and 75 μm sieves. The granules were sieved to the desired particle size requirements. In particular, no granules had a particle size greater than 850 μm. At least 90% by weight of the granules had a particle size of from 75 to 850 μm. Not more than 5% by weight of the granules had a particle size of greater than 500 μm. The oversized and undersized granules were used.

Each powder has the following further properties:

(i) the granules disintegrate within 30 minutes according to the Disintegration Test of The Pharmacopoeia of Japan, twelfth edition, 1991, and
(ii) at least 90% by weight of the lamotrigine dissolves within 30 minutes according to the Dissolution Test, method 2 (paddle method) of The Pharmacopoeia of Japan, twelfth edition, 1991.

We claim:

1. A pharmaceutical formulation which comprises:
   (a) from 0.5 to 50% by weight of lamotrigine or a pharmaceutically acceptable acid addition salt thereof,
   (b) from 15 to 50% by weight of lactose,
   (c) from 15 to 50% by weight of starch,
   (d) from 0.5 to 15% by weight of crystalline cellulose, and
   (e) from 5 to 15% by weight of polyvinylpyrrolidone,
   and which is in the form of a free-flowing powder of granules having the following properties:
      (i) no granules have a particle size of greater than 850 μm,
      (ii) at least 90% by weight of the granules have a particle size of from 75 to 850 μm,
      (iii) the granules disintegrate within 30 minutes, and
      (iv) at least 90% by weight of the lamotrigine or lamotrigine salt in the granules dissolves within 30 minutes.

2. A formulation according to claim 1, which comprises:
   (a') from 0.5 to 15% by weight of lamotrigine or a lamotrigine salt,
   (b') from 35 to 45% by weight of lactose,
   (c') from 35 to 45% by weight of corn starch,
   (d') from 3.5 to 6% by weight of crystalline cellulose, and
   (e') from 6 to 9% by weight of polyvinylpyrrolidone.

3. A formulation according to claim 2, which comprises 1% by weight of lamotrigine, 43% by weight of each of lactose and starch, 5% by weight of crystalline cellulose and 8% by weight of polyvinylpyrrolidone.

4. A formulation according to claim 2, which comprises 10% by weight of lamotrigine 38.5% by weight of each of lactose and starch, 5% by weight of crystalline cellulose and 8% by weight of polyvinylpyrrolidone.

5. A formulation according to claim 1, wherein not more than 5% by weight of the granules have a particle size of greater than 500 μm.

6. A formulation according to claim 1, wherein the powder has a bulk density of from 0.36 to 0.40 g/cm$^3$.

7. A formulation according to claim 1, wherein the starch is corn starch.

8. A process for the preparation of a pharmaceutical formulation which comprises
   (a) from 0.5 to 50% by weight of lamotrigine or a pharmaceutically acceptable acid addition salt thereof,
   (b) from 15 to 50% by weight of lactose,
   (c) from 15 to 50% by weight of starch,
   (d) from 0.5 to 15% by weight of crystalline cellulose, and
   (e) from 5 to 15% by weight of polyvinylpyrrolidone,
   and which is in the form of a free-flowing powder of granules having the following properties.
      (i) no granules have a particle size of greater than 850 μm,
      (ii) at least 90% by weight of the granules have a particle size of from 75 to 850 μm,
      (iii) the granules disintegrate within 30 minutes
      (iv) at least 90% by weight of the lamotrigine or lamotrigine salt in the granules dissolves within 30 minutes which process comprises spray-granulating the lamotrigine or lamotrigine salt, lactose, corn starch and crystalline cellulose in the presence of, as a binder, polyvinylpyrrolidone.

* * * * *